United States Patent [19]

Sinclair

[11] Patent Number: 4,897,383

[45] Date of Patent: Jan. 30, 1990

[54] AVERMECTIN DERIVATIVES

[75] Inventor: Peter J. Sinclair, Suffern, N.Y.

[73] Assignee: Merck & Co., Inc., Rahway, N.J.

[21] Appl. No.: 309,569

[22] Filed: Feb. 13, 1989

[51] Int. Cl.$^4$ .................. A61K 31/71; C07H 17/08
[52] U.S. Cl. ................................ 514/30; 536/71; 549/209
[58] Field of Search .................. 549/264; 536/7.1; 514/30

[56] References Cited

U.S. PATENT DOCUMENTS

| | | | |
|---|---|---|---|
| 4,199,569 | 4/1980 | Chabela et al. | 536/7.1 |
| 4,206,205 | 6/1980 | Mrozik et al. | 536/7.1 |
| 4,310,519 | 1/1982 | Albers-Schonberg | 536/7.1 |

FOREIGN PATENT DOCUMENTS

| | | | |
|---|---|---|---|
| 276131 | 1/1987 | European Pat. Off. | 536/7.1 |
| 214731 | 3/1987 | European Pat. Off. | 536/7.1 |
| 276103 | 7/1988 | European Pat. Off. | |

OTHER PUBLICATIONS

Chen et al., Abstracts of Papers–American Chemical Society, 196 Meeting MBTD 28 (1983).
Shulman et al., (I) *Antimicrobial Agents and Chemotherapy* 31, pp. 744–747 (1987).
Fisher et al., *Macrolide Antibiotics* Omura (Ed) Academic Press, New York, N.Y., pp. 553–606 (1984).
Davies et al., *Natural Products Reporter 3*, pp. 87–121 (1986).

*Primary Examiner*—Richard L. Raymond
*Assistant Examiner*—Mark W. Russell
*Attorney, Agent, or Firm*—David L. Rose; Hesna J. Pfeiffer

[57] ABSTRACT

There are disclosed novel avermectin derivatives wherein the 3″- or 3′-methoxy group and/or the 4″- or 4′-hydroxyl group are replaced by hydrogen. The 3″- or 3′-desmethoxy-avermectins can further be derivatized at the 4″- or 4′-positions as the amino, semicarbazone or oxime analogs. The 3″- or 3′-desmethoxy-avermectins are prepared by the reaction of Samarium iodide on the corresponding 4″- or 4′-oxo-avermectins. The 4″- or 4′-deoxo-avermectins are prepared by radical deoxygenation of the corresponding hydroxy-avermectins. Di-deoxygenated avermectin derivatives are obtained by combination of these two methods or by treating avermectin aglycone or avermectin monosaccharide with a dihydropyran. The new compounds are potent anti-parasitic agents, in particular, the compounds are anthelmintic, insecticidal and acaricidal agents.

18 Claims, No Drawings

AVERMECTIN DERIVATIVES

BACKGROUND OF THE INVENTION

The term avermectin (previously referred to as C-076) is used to describe a series of compounds isolated from the fermentation broth of an avermectin producing strain of Streptomyces avermitilis and derivatives thereof. The morphological characteristics of the culture are completely described in U.S. Pat. No. 4,310,519. The avermectin compounds are a series of macrolides, each of which is substituted at the 13 position with a 4-(α-L-oleandrosyl)-α-L-oleandrose group. The avermectin compounds and the instant derivatives thereof have a very high degree of anthelmintic and anti-parasitic activity.

The avermectin series of compounds isolated from the fermentation broth have the following structure:

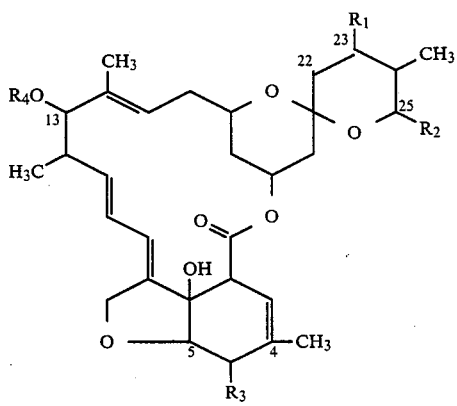

wherein $R_4$ is the 4'-(α-L-oleandrosyl)-α-L-oleandrosyl group of the structure:

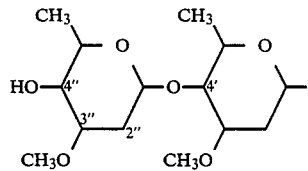

and wherein the broken line indicates a single or a double bond;

$R_1$ is a hydrogen or hydroxy and is present only when said broken line indicates a single bond;

$R_2$ is iso-propyl or sec-butyl; and $R_3$ is methoxy or hydroxy.

There are eight different avermectin natural product compounds and they are given the designations A1a, A1b, A2a, A2b, B1a, B1b, B2a, and B2b based upon the structure of the individual compounds.

In the foregoing structural formula, the individual avermectin compounds are as set forth below. (The $R_4$ group is 4''-(α-L-oleandrosyl)-α-L-oleandrose):

|     | $R_1$ | $R_2$ | $R_3$ |
| --- | --- | --- | --- |
| A1a | (22,23-double bond) | sec-butyl | —OCH$_3$ |
| A1b | (22,23-double bond) | iso-propyl | —OCH$_3$ |
| A2a | —OH | sec-butyl | —OCH$_3$ |
| A2b | —OH | iso-propyl | —OCH$_3$ |
| B1a | (22,23-double bond) | sec-butyl | —OH |
| B1b | (22,23-double bond) | iso-propyl | —OH |
| B2a | —OH | sec-butyl | —OH |
| B2b | —OH | iso-propyl | —OH |

The avermectin compounds are generally isolated as mixtures of a and b components. Such compounds differ only in the nature of the $R_2$ substituent and the minor structural differences have been found to have very little effect on the isolation procedures, chemical reactivity and biological activity of such compounds.

In addition to these natural avermectins containing the 25-iso-propyl or 25-sec-butyl-substituent, closely related derivatives containing other branched or cyclic 25-alkyl or 25-alkenyl substituents, optionally further substituted by heteroatoms such as oxygen, sulfur, nitrogen, halogen, are known in the literature. These derivatives are obtained through various adjustments and additions to the fermentation procedures as described fully in the European Patent Application EPO 0 214 731.

Avermectins are products of microbial fermentations using the actinomycete Streptomyces avermitilis. These microbes use acetates and propionates as building blocks for most of the avermectin carbon chain, which is then further modified by microbial enzymes to give the completed avermectin molecules. It is known, however, that the carbon C-25 and the 2-propyl and 2-butyl substituents at this carbon are not derived from acetate or propionate units, but are derived from aminoacids L-valine and L-isoleucine, respectively. It was also found, that these aminoacids are deaminated to the corresponding 2-ketoacids, and that these then are decarboxylated to give 2-methylpropionic and 2-methylbutyric acids. These acids are then directly incorporated into the avermectin structures to give the 2-propyl and 2-butyl C-25 substituents, as is reported by Chen et al., Abstr. Pap. Am. Chem. Soc. (186 Meet., MBTD 28, 1983). It was also disclosed in European Patent Application number 0 214 731 that additions of large amounts of other acids such as cyclopentanoic, cyclobutyric, 2-methylpentanoic, 2-methylhexanoic, thiophene-3-carboxylic acids and others to the fermentation broth of S. avermitilis causes the microbes to accept these acids as substitutes and to make small amounts of avermectins containing these acids in form of new C-25 substituents. Examples of such new avermectin derivatives are:

25-(thien-3-yl)-25-de-(1-methylpropyl)avermectin A2a
25-(cyclohex-3-enyl)-25-de-(1-methylpropyl)avermectin A2a
25-cyclohexyl-25-de-(1-methylpropyl)avermectin A2a
25-(1-methylthioethyl)-25-de-(1-methylpropyl)avermectin A2a
25-(2-methylcyclopropyl)-25-de-(1-methylpropyl)avermectin A2a Still additional avermectin derivatives are produced through artificial modification of the fermentation of Streptomyces avermitilis either by addition of metabolic inhibitors such as sinefungin (as described by Schulman et al., J. Antibiot. 1985, 38, 1494–1498) or by mutation of the parent strain (as described by Schulman et al., Antimicrobial Agents and Chemotherapy, 1987, 31, 744–747, and by EP-276-131-A to Pfizer INC.). Some of these avermectin derivatives are still further modified and are missing one or two of the 3'- and 3''-O-methyl groups (Schulman et al., J. Antibiot. 1985, 38, 1494–1498). Examples for such derivatives are:

3',3''-O-Bisdesmethylavermectin B1a/B1b
3',3''-O-Bisdesmethylavermectin B2a/B2b
3''-O-Desmethylavermectin B1a/B1b
3',3''-Bisdesmethyl-25-cyclohexyl-25-de-(2-butyl)-avermectin B2a
3',3''-Bisdesmethyl-25-cyclopentyl-25-de-(2-butyl)-avermectin B2a
3',3''-Bisdesmethyl-25-(3-thienyl)-25-de-(2-butyl)-avermectin B2a
3',3''-Bisdesmethyl-25-(3-furyl)-25-de-(2-butyl)-avermectin B2a
3',3''-Bisdesmethyl-25-(1-methylthioethyl)-25-de-(2-butyl)-avermectin B1a.

The fermentation products have been chemically modified in order to obtain further antiparasitic and insecticidal analogs with improved properties. Publications of such procedures in the scientific and patent literature have been reviewed by Fisher, M. H.; Mrozik, H. *Macrolide Antibiotics*; Omura, S., Ed.; Academic Press: New York, 1984; pp 553–606, and by Davies, H. G.; Green, R. H. *Nat. Prod. Rep.*, 1986, 3, 87–121.

For example a group of semisynthetic avermectin derivatives were obtained by hydrogenating specifically the 22,23-double bond of avermectin $B_1$ compounds giving 22,23-dihydroavermectin $B_1$ derivatives which have very potent anthelmintic and antiparasitic properties. Other examples of semisynthetic avermectin derivatives contain a 8,9-oxide group, a 4a-hydroxy or acyloxy group, a 23-keto group, which all are potent antiparasitic and insecticidal compounds.

These compounds may be used as starting materials for the compounds of the instant invention without further modification, or when containing additional reactive groups, which are not to be modified under the reaction conditions applied, only after protection of such with a suitable protecting group.

SUMMARY OF THE INVENTION

The instant invention is concerned with derivatives of avermectin compounds wherein the 3''- or 3'-methoxy group and or the 4''- or 4'-hydroxy group is removed. The deoxygenated compounds are then further modified at other functionalities. Thus it is the object of this invention to describe such compounds. It is a further object of this invention to describe the processes useful for the preparation of such compounds. A still further object is to describe the use of such compounds as anthelmintic, insecticidal, and acaricidal agents. Still further objects will become apparent from the reading of the following description.

DESCRIPTION OF THE INVENTION

The compounds of the instant invention have the following structural formula:

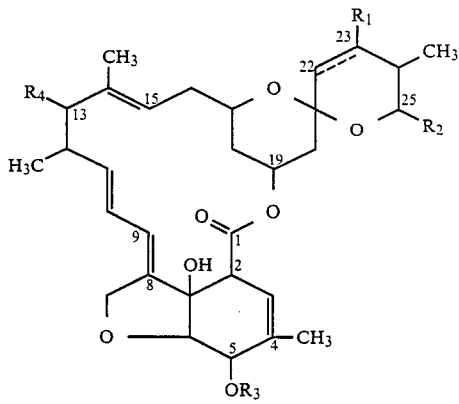

wherein the broken line at the 22,23 position represents a 22,23-single bond and wherein $R_1$ is hydrogen, hydroxy or keto, or the broken line represents a 22,23-double bond and $R_1$ is absent;

$R_2$ is an alpha-branched $C_3$–$C_8$ alkyl or alkenyl group;

$R_3$ is hydrogen, loweralkyl or loweralkanoyl;

$R_4$ is

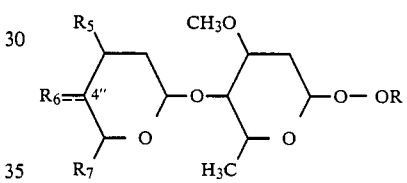

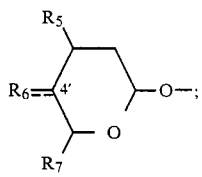

$R_5$ is hydrogen and $R_6$ is hydroxy, amino, N-loweralkylamino, N,N-diloweralkylamino, loweralkanoylamino or N,N-diloweralkylalkanoylamino, when the broken line to $R_6$ indicates a 4' or 4'' single bond or $R_6$ is keto, semicarbazone, N-loweralkylsemicarbazone, N,N-diloweralkylsemicarbazone, oxime, or loweralkyloxime when the broken line to $R_6$ indicates a 4' or 4'' double bond;

or $R_5$ is hydrogen or methoxy and $R_6$ is hydrogen; and $R_7$ is methyl or hydrogen.

Preferred compounds of the instant invention are realized in the foregoing structural formula wherein the the broken line at the 22,23 position represents a single bond and wherein $R_1$ is hydrogen or hydroxy, or the broken line represents a double bond and $R_1$ is absent;

$R_2$ iso-propyl, sec-butyl, or an alpha-branched $C_3$–$C_8$ alkenyl group;

$R_3$ is hydrogen $R_4$ is

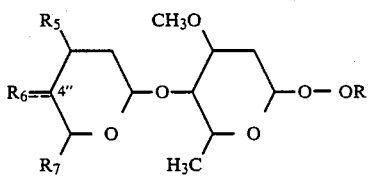

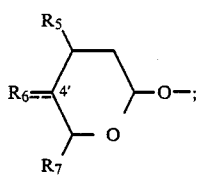

$R_5$ is hydrogen and $R_6$ is hydroxy, amino, N-loweralkylamino, loweralkanoylamino, or N,N-diloweralkylalkanoylamino, when the broken line to $R_6$ indicates a 4' or 4" single bond or $R_6$ is keto, semicarbazone, N-loweralkylsemicarbazone, N,N-diloweralkylsemicarbazone, or oxime when the broken line to $R_6$ indicates a 4' or 4" double bond; or $R_5$ is hydrogen or methoxy and $R_6$ is hydrogen, and $R_7$ is methyl or hydrogen.

The most preferred compounds are realized in the foregoing structural formula wherein the broken line at the 22,23 position represents a single bond and wherein $R_1$ is hydrogen or hydroxy, or the broken line represents a double bond and $R_1$ is absent;

$R_2$ iso-propyl, sec-butyl, or an alpha-branched $C_3$–$C_8$ alkenyl group;

$R_3$ is hydrogen $R_4$ is

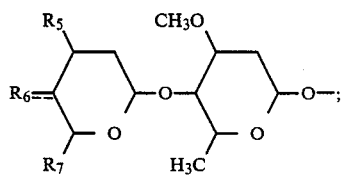

$R_5$ is hydrogen;

$R_6$ is hydrogen, hydroxy, amino, N-loweralkylamino, loweralkanoylamino, or N,N-diloweralkylalkanoylamino, when the broken line to $R_6$ indicates a 4' or 4" single bond or $R_6$ is keto, semicarbazone, N-loweralkylsemicarbazone, N,N-diloweralkylsemicarbazone, or oxime when the broken line to $R_6$ indicates a 4' or 4" doublebond; and $R_7$ is methyl or hydrogen.

Preferred compounds of the instant invention are further realized in the following compounds:
4"-oxo-3"-desmethoxy avermectin B1a/B1b
3"-desmethoxy-4"-epi avermectin B1a/B1b
3"-desmethoxy avermectin B1a/B1b
4'-0-tetrahydropyranyl-avermectin B1a/B1b monosaccharide
3"-desmethoxy-4"-deoxo-4"-methylamino-avermectin B1a/B1b
3"-desmethoxy-4"-deoxo-4"-epi-methylamino-avermectin B1a/B1b
4"-amino-4"-deoxo-3"-desmethoxy–avermectin B1a/B1b
4"-deoxo-3"-epi-amino-avermectin B1a/B1b
4"-acetylamino-4"-deoxo-3"-desmethoxy-avermectin B1a/B1b
4"-deoxo-3"-desmethoxy-4"-epi-acetylamino-avermectin B1a/B1b
3"-desmethoxy avermectin B1a/B1b-4"-semicarbazone
4"-deoxo-22,23-dihydro-avermectin B1a/B1b
3"-desmethoxy-22,23-dihydro-4"-oxo-avermectin B1a/B1b
3"-desmethoxy-22,23-dihydro-avermectin B1a/B1b
3"-desmethoxy-22,23-dihydro-4"-epi-avermectin B1a/B1b
3"-desmethoxy-22,23-dihydro-4"-deoxo-4"-methylamino-avermectin B1a/B1b
3'-desmethoxy-4'-deoxo-4'-methylamino-avermectin B1a/B1b monosaccharide
4"-amino-4"-deoxo-3"-desmethoxy-avermectin B2a/B2b
25-cylopentyl-25-de-(1-methylpropyl)-3"-desmethoxy-4"-oxo-avermectin B2a
25-cylopentyl-25-de -(1-methylpropyl)-3"-desmethoxy-avermectin B1a
25-cylopentyl-25-de-(1-methylpropyl)-3"-desmethoxy-4"-epi-avermectin B1a In the instant invention the term "loweralky" is intended to indicate those alkyl groups of from 1 to 6 carbon atoms such as methyl, ethyl, propyl, isopropyl, butyl, pentyl, hexyl, and the like The term "loweralkoxy" is intended to include those alkoxy groups of from 1 to 6 carbon atoms such as methoxy, ethoxy, propoxy, isopropoxy, butoxy, pentoxy, hexoxy, and the like.

The term "loweralkanoyl" is intended to include those alkanoyl groups of from 1 to 6 carbon atoms such as formyl, acetyl, propionyl, butyryl, pentanoyl, hexanoyl, and the like.

The term "halogen" is intended to include the halogen atoms, fluorine, chlorine, bromine, or iodine.

The "b" compounds, those with a 25-iso-propyl group, may be somewhat difficult to separate from the corresponding "a" compound with a 25-sec-butyl group and as such the compounds are generally isolated as mixture of the two compounds. Thus references in the instant application to "a" compounds such as B1a, A1a, and the like, are construed to actually contain a certain proportion of the corresponding "b" compound. Alternatively, this representation of a mixture is sometimes done by referring to the B1 or B2 compounds without specifically designating "a" or "b" compounds, or by separating the "a" compound from the "b" compound by a slash (/) such as B1a/B1b, B2a/B2b and the like.

The above structural formula is shown without a definitive stereochemistry. However, during the course of the synthetic procedures used to prepare such compounds, or using racemization or epimerization procedures known to those skilled in the art the products of such procedures can be a mixture of stereoisomers. In particular, the stereoisomers at the 13- and 23-positions may be oriented either α- or β- representing such groups belong below or above the general plane of the molecule, respectively. In each such case both the α- and β- configurations are intended to be included within the ambit of this invention.

PREPARATION OF STARTING MATERIALS

The ultimate starting materials for the compounds of this invention are the avermectin fermentation products defined above. In addition other microbially produced avermectin derivatives containing an alpha branched alkyl or alkenyl group substituent at the 25 position designated in the structural formula as $R_2$ have been described in European patent application No. 86305604.0 (publication No. 0 214 731), 88300426.9 (0 276 131), and 88300354.3 (0 276 103). These compounds can also be used as starting materials for the compounds claimed in this invention. The $R_2$ substituent is inert under the reaction conditions employed for the preparation of the compounds of this invention, so that these reactions can also be carried out with these altered avermectin derivatives. It is apparent that additional reactions are required to prepare the instant compounds. Specifically, reactions are carried out at the 5, 22, and 23-positions. It is generally preferred to prepare whatever substituents are required at these positions before the oxidation at the 4''-hydroxy and subsequent substitution on the thus produced 4''-ketone. Such a procedure generally avoids undesirable side reactions. This technique is not required, however, and if desired other sequences may be used. In addition, during the oxidation and substitution reaction described above, it is necessary to protect the hydroxy group at the 5-position to avoid oxidation or substitution at such position. With this position protected the reactions may be carried out at the 4''- or 4'-positions without affecting the remainder of the molecule. Subsequent to any of the above described reactions the protecting group may be removed and the unprotected product isolated. The protecting group employed is ideally one which may be readily synthesized, will not be affected by the reactions at the 4''- and 4'-positions and may be removed without affecting any other functionality of the molecule. One preferred type of protecting group for the avermectin type of molecule is the tri-subsituted silyl group, preferably the trialkyl silyl group. One especially preferred example is the t-butyldimethylsilyl group. The reaction preparing the protected compound is carried out by reacting the hydroxy compound with the appropriately substituted silylhalide, preferably the silylchloride in an aprotic solvent such as methylene chloride, benzene, toluene, ethyl acetate, tetrahydrofuran, dimethylformamide and the like. In order to minimize side reactions, there is included in the reaction mixture a base to react with the acid halide released during the course of the reaction. Preferred amines are imidazole, pyridine, or triethylamine. The base is required in amounts equimolar to the amount of hydrogen halide liberated; however, generally several equivalents of the amine are employed. The reaction is stirred at from 0° C. to the reflux temperature of the reaction mixture and is complete in from ½ to 16 hours.

The silyl group is removed by stirring the silyl compound in methanol catalyzed by an acid preferably a sulfonic acid monohydrate such as p-toluenesulfonic acid monohydrate. The reaction is complete in about ½ to 12 hours at from 0° to 50° C. Alternatively, the silyl group may be removed by treatment of the silyl compound with anhydrous pyridine-hydrogen fluoride in tetrahydrofuran. The reaction is complete in from 3 to 24 hours at from 0° to 25° C.

Another of the starting materials used in the foregoing reaction scheme are those in which the 22,23, double bond has been reduced to a single bond. The preferred catalyst for the selective hydrogenation of the 22,23 double bond is one having the formula:

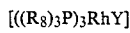

$[((R_8)_3P)_3RhY]$ wherein $R_8$ is loweralkyl, phenyl, or loweralkyl substituted phenyl and Y is halogen. The reduction is completely described in U.S. Pat. No. 4,199,569.

The other starting materials which are used in the above reaction scheme involve the preparation of the monosaccharide. The processes which may be used to prepare the monosaccharide derivatives of the avermectin compounds are described in U.S. Pat. No. 4,206,205. The reaction consists generally of treating the starting disaccharide with acid in an aqueous organic solvent mixture. Water concentration of from 0.1 to 20% by volume and acid concentrations of from about 0.01 to 1.0% will predominantly produce the monosaccharide.

A further procedure for the preparation of the monosaccharide utilizes a 1% mineral acid solution in isopropanol at 20° to 40° C. for from 6 to 24 hours. Mineral acids such as sulfuric, phosphoric, and the like may be employed.

In all cases the substituent at the 25-position of the avermecin is inert to the reaction conditions and the presence of alkyl groups, alkenyl groups, cycloalkyl groups, cycloalkenyl groups and the like at this position will little affect the preparation, isolation, or activity of the avermectin derivative.

PREPARATION OF COMPOUNDS

The preparation of the instant compounds requires that the avermectin starting materials are oxidized at the 4'- or 4''-position to the corresponding ketones. During the procedure the presence of a hydroxy group at the 5-position will require that such group be protected in order that it too is not oxidized. The 23-hydroxy group is less reactive and the 7-hydroxy group is very unreactive and they need not be protected. The procedure used to prepare the protected intermediates are described above. The oxidation reaction is carried out in an inert solvent such as methylene chloride using oxalyl chloride or trifluoroacetic anhydride and dimethylsulfoxide as the oxidizing agent. Additionaly, N-chlorosuccinimide and dimethylsulfide may be employed. The reaction proceeds by dissolving the oxalyl chloride or trifluoroacetic anhydride and dimethylsulfoxide (or other oxidizing agent) in methylene chloride with cooling from −50° to −80° C. and adding dropwise a methylene chloride solution of the avermectin compound to be oxidized. The addition is carried out over a period of from 15 minutes to 1 hour and then triethylamine is added dropwise over a period of from 1 to 15 minutes. The reaction mixture is then allowed to warm to room temperature over a period of from ½ to 1 hour. The 4''- or 4''-keto compound is isolated using techniques known to those skilled in the art.

Preparation of the 3''-desmethoxy-4''-oxo-avermectin is carried out by treatment of the corresponding 4''-oxo-avermectin, either protected or unprotected at the 5-position, with a reducing agent such as samarium diiodide or ytterbium diiodide in an organic solvent such as THF, ether, benzene and the like in the presence of a proton doner such as methanol, ethanol, propanol, butanol and the like at temperatures ranging from −100° C. to 25° C. for 0.25-2 h. The compound is isolated and purified by techniques known to those skilled in the art.

The 3''-desmethoxy avermectin and 3''-desmethoxy-4''-epi-avermectin analogs are prepared by treatment of the corresponding 4''-keto compound with a hydride source such as sodium borohydride, sodium cyanoborohydride and the like in a protic solvent such as methanol, ethanol and the like at temperatures ranging from −20° C. to 30° C. The compounds are isolated and purified by techniques known to those skilled in the art.

The 3″-desmethoxy-4″-keto-avermectin is aminated to prepare the unsubstituted amino compound. The reaction is carried out in an inert solvent such as methanol at from −10° and +25° C. using ammonium salts such as ammonium acetate or ammonium chloride and sodium cyanoborohydride as the aminating and reducing reagents. The reaction is complete in from 15 minutes to 2 hours and the product 3″-desmethoxy-4″deoxy-4″-amino compound is isolated by techniques known to those skilled in the art.

As a variation to the foregoing amination reaction, alkyl ammonium salts could be used in place of the ammonium salts to prepare the mono alkyl substituted compounds directly. The same reagents, salts and conditions as described above can be used for such a reaction.

The substitution reaction at the newly formed amino group wherein the substituent is an acyl functionality is carried out using an acylating reagent in the presence of a base in an inert solvent. The preferred acylating reagents are loweralkanoyl anhydrides, loweralkanoyl halides, substituted benzenesulfonyl chlorides, loweralkyl sulfonyl chlorides and the like. The reaction is carried out in an inert solvent such as methylene chloride in the presence of a non-reactive base such as pyridine or triethylamine in order to neutralize the acid produced during the course of the reaction. The reaction temperature is from −10° to 25° C. and the reaction is complete in from 5 minutes to 1 hour. The product is isolated using known techniques.

Preparation of 3″-desmethoxy-4″-deoxo-avermectin-4″-semicarbazones is carried out by treatment of 3″-desmethoxy-4-oxo-avermectin $B_1$ with a semicarbazide in a polar solvent such as methanol, ethanol, tetrahydrofuran, and the like in the presence of catalytic acid, preferably acetic acid, at temperatures ranging from −20° to 30° C. for a period of 0.5 to 20 h affords the corresponding semi-carbazone isolated and purified by techniques known to those skilled in the art. Likewise 3″-desmethoxy 4″-oxo-avermectin $B_1$ oximes can be prepared in a similar manner substituting hydroxylamine or an O-substituted-hydroxylamine for the semicarbazide.

The tetrahydropyranyl derivative is prepared by treatment of 5-O-tert-butyldimethylsilyl-avermectin $B_1$ monosaccharide with dihydropyran in a non-nucleophilic aprotic solvent such as methylene chloride, chloroform, benzene, ether, tetrahydrofuran and the like in the presence of a catalyst such as pTsOH, $ZnCl_2$, camphorsulphonic acid and the like at temperatures ranging from −20° to 50° C. from 0.5 to 12 h. The product is isolated and purified by techniques known to those skilled in the art. The silyl group is removed as previously described to give the tetrahydropyranyl compound.

All of the foregoing reactions carried out at the 4″-position of the avermectin can be carried out at the 4′-position of the monosaccharide to afford the corresponding monosaccharide derivatives.

The novel compounds of this invention have significant parasiticidal activity as anthelmintics, ectoparasiticides, insecticides, and acaracides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats, and poultry. Among the helminths the group of worms described as nematodes causes widespread and oftentimes serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictocaulus, Capillaria, Heterakis, Toxocara, Ascaridia, Oxyuris, Ancylostoma, Uncinaria, Toxascaris, and Parascaris. Certain of these, such as Nematodirus, Cooperia, and Oesophagostomum attack primarily the intestinal tract while others, such as Haemonchus and Ostertagia, are more prevalent in the stomach while still others such as Dictocaulus are found in the lungs. Still other parasites may be located in other tisues and organs of the body such as the heart and blood vessels, subcutaneous and lymphatic tissue and the like. The parasitic infections known as helminthiasis lead to anemia, malnutrition, weakness, weight loss, severe damage to the walls of the intestinal tract and other tissues and organs and, if left untreated, may result in the death of the infected host. The avermectin compounds of this invention have unexpectedly high activity against Dirofilaria in dogs, Nematospiroides, Syphacia, Aspiculuris in rodents, anthropod ectoparasites of animals and birds such as ticks, mites, lice, fleas, blowfly, in sheep Lucilia sp., biting insects and such migrating dipterous larvea as Hypoderma sp. in cattle, Gastrophilus in horses, and Cuterebra sp. in rodents.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal trct are the filiarial worms such as Wuchereria, Brugia, Onchocerca and Loa, Dracunculus and extra-intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., and the housefly *Musca domestica*.

The compounds are also useful against insect pests of stored grains such as Tribolium sp., Tenebrio sp. and of agricultural plants such as spider mites (Tetranychus sp.) aphids (Acyrthiosiphon sp.); against migratory orthopterans such as locusts and immature stages of insects living on plant tissue. The compounds are useful as a nematocide for the control of soil nematodes and plant parasites such as Meloidogyne spp, which may be of importance in agriculture.

These compounds may be administered orally in a unit dosage form such as a capsule, bolus or tablet, or as a liqid drench where used as an anthelmintic in mammals. The drench is normally a solution, suspension or dispersion of the active ingredient usually in water together with a suspending agent such as bentonite and a wetting agent or like excipient. Gradually, the drenches also contain an antifoaming agent. Drench formulations generally contain from about 0.001 to 5% by weight of the active compound. Preferred drench formulations may contain from 0.01 to 0.1% by weight active compound. The capsules or boluses are comprised of the active ingredient admixed with a carrier vehicle such as starch, talc, magnesium stearate, or di-calcium phosphate.

Where it is desired to administer the avermectin derivatives in a dry, solid unit dosage form, capsules, boluses, or tablets containing the desired amount of active compound usually are employed. The dosage forms are prepared by intimately and uniformly mixing the active ingredients with suitable finely divided diluents, fillers, disintegrating agents, and/or binders such as starch, lactose, talc, magnesium stearate, vegetable gums and the like. Such unit dosage formulations may be varied widely with respect to their total weight and content of antiparasitic agent depending upon factors such as the type of host animal to be treated, the severity and type of the infection and the weight of the host.

When the active compound is to be administered via the animal feedstuff, it is intimately dispersed in the feed or used as a top dressing or in the form of pellets which may then be added to the finished feed or optionally fed separately. Alternatively, the antiparasitic compounds of our invention may be administered to the animals parenterally, for example, by intraruminal, intramuscular, intratracheal, or subcutaneous injection in which the active ingredient is dissolved or dispersed in a liquid carrier vehicle. For parenteral administration, the active material is suitably admixed with an acceptable vehicle, preferably of the vegetable oil variety such as peanut oil, cotton seed oil, and the like. Other pareteral vehicles such as organic preparation using solketal, glycerol formal, and aqueous parental formulations are also used. The active avermectin compound or compounds are dissolve or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites, and other biting insects in domesticated animals and poultry. They are also effective in treatment of parasitic diseases that occur in other animals including humans. The optimum amount to be employed for the best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1-5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field. When the compounds described herein are asministered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for the direct feeding to the animal or for addition to the feed either directly or after an intermediate dilution or blending step. Typical carriers or diluents suitable for such compositions include, for example, distillers' dried grains, corn meal, citrus meal, fermentaion residues, ground oyster shells, wheat shorts, molasses solubles, corn cob meal, edible bean mill feed, soya grits, crushed limestone and the like. The active avermectin compounds are intimately dispersed throughout the carrier by methods such as grinding, stirring, milling, or tumbling. Compositions containing from about 0.005 to 2.0% weight of the active compound are particularly suitable as feed premixes. Feed supplements, which are fed directly to the animal, contain from about 0.002 to 0.3% by weight of the active compounds.

Such supplements are added to the animal feed in an amount to give the finished feed the concentration of active compound desired for the treatment and control of parasitic diseases. Although the desired concentration of the active compound will vary depending upon the factors previously mentioned as well as upon the particular avermectin derivative employed, the compounds of this invention are usually fed at concentrations of between 0.00001 to 0.002% in the feed in order to achieve the desired antiparasitic result.

In using the compounds of this invention, the individual avermectin components may be prepared and used in that form. Alternatively, mixtures of two or more of the individual avermectin components may be used, or other active compounds not related to the compounds of this invention.

The compounds of this invention are also useful in combatting agricultural pests that inflict damage upon crops while they are growing or in storage. The compounds are applied using known techniques as sprays, dusts, emulsions and the like, to the growing or stored crops to effect protection from such agricultural pests.

The following examples are provided in order that this invention might be more fully understood; they are not to be construed as limitative of the invention.

The avermectin derivatives prepared in the following examples are generally isolated as amorphous solids and not as crystalline solids. They are thus characterized analytically using techniques such as mass spectrometry, nuclear magnetic resonance spectrometry and the like. Being amorphous, the compounds are not characterized by sharp melting points, however, the chromatographic and analytical methods employed indicate that the compounds are pure.

EXAMPLE 1

3''-desmethoxy-4''-oxo-5-O-tert butyldimethyl avermectin B1a/B1b

To a dry 250 mL. 3-neck round bottom flask equipped with a 250 mL. addition funnel, a nitrogen inlet and a teflon coated stir bar was added Samarium metal (750 mg., 5 mmol., 2.5 eq.). The addition funnel was charged with dry THF (110 mL.). To the THF was added 1,2-diiodoethane (1.18 g., 4.2 mmol., 2.1 eq.). The diiodoethane solution was added dropwise to the Samarium metal over 45 min at room temperature under $N_2$. After addition was complete the deep blue mixture was stirred for 30 min then cooled to $-78°$ C. in a dry ice/acetone bath. 4''-Oxo-5-O-t-butyldimethylsilyl avermectin B1a/B1b (1.96 g., 2.0 mmol., 1 eq.) was dissolved in dry THF (4 mL.) and methanol (2 mL.) in a 25 mL. pear-shaped flask. The avermectin solution was cooled to $-78°$ C. under nitrogen and transferred via cannula to the flask containing the $SmI_2$ solution. After 25 min the mixture was still dark blue. The cooling bath was removed and the reaction was allowed to warm. After an additional 20 min the reaction mixture was poured into a separatory funnel containing aqueous $NaHCO_3$ and extracted 5x with $CH_2Cl_2$. The organic extracts wre combined and dried over anhydrous $Na_2SO_4$. The mixture was filtered, concentrated in vacuo and separated by flash column chromatography on silica gel (eluted with 7:1 hexanes/acetone to afford 550 mg 3''-desmethoxy-4''oxo-5-O-tert-butyldimethyl avermectin $B_1$ as a white solid characterized by $^1H$ NMR spectral data. Selected $^1H$ NMR data (300 MHz)($CDCl_3$)δ $CHCl_3$: 4.27(1H, q, J=6.5 Hz, H5''); 4.9(1H, s, C7 OH); 3.44(3H, s, 3'-$OCH_3$); 0.9(9H, s, $SiCMe_3$); 0.11(6H, s, $SiCH_3$).

EXAMPLE 1A

3''-dimethoxy-22,23-dihydro-4''oxo-5-O-tert-butyldimethyl avermectin B1a/B1b

A solution of 22,23-dihydro-4''oxo-5-O-tert-butyldimethyl avermectin B1a/B1b (1.96 g) and methanol (2 mL.) in Tetrahydrofuran (110 mL.) is reacted with samarium diiodide solution in tetrahydrofuran (110 mL., 0.04M solution) in accordance with the procedure described fully in example 1 to give 3''-desmethoxy-22,23-dihydro-4''-oxo-5-O-tert-butyldi-methyl avermectin B1a/B1b

EXAMPLE 2

3''-desmethoxy-4''-oxo avermectin B1a/B1b

To a strirred solution of 3''-desmethoxy-4''oxo-5-O-tert-butyldimethylsilyl avermectin B1a/B1b (300 mg., 0.315 mmol., 1 eq.) in methanol (5 mL.) and water (2 mL.) at 0° C. was added a solution of p-TsOH in methanol (5 mL., 1% by weight p-TsOH). The solution was stirred at 0° C. for 7.5 h, stored at $-4°$ C. for 14 h, and then placed in an ice bath and allowed to slowly warm to room temperature over 6 h. The reaction mixture was quenched with aqueous $NaHCO_3$ and extracted 4x with $CH_2Cl_2$. The organic extracts were combined, dried over anhydrous $Na_2SO_4$, filtered, concentrated in vacuo, and separated by flash column chromatography (eluted with 6:1 hexanes/acetone) to afford 192.8 mg 3''-desmethoxy-4''-oxo-avermectin B1a/B1b characterized by $^1H$ NMR, UV, and mass spectral analysis. Selected $^1H$ NMR data (300 MHz)($CDCl_3$) δ $CHCl_3$: 4.22–4.31(1H, q, C5''); 4.22–4.31(1H, buried, C5); 4.0 (1H, s, C7-OH); 3.44(3H, s, 3'-$OCH_3$); 3.37(1H, t, J=8 Hz, C4'H); 3.27(1H, m, C2H); 1.27(3H, d, J=7.5 Hz, C5'Me); 1.22(3H, d, J=6 Hzm, C5''Me); 1.13(3H, d, J=6.5, C24Me). Mass spectrum (FAB)(Li spike): 847($M^+ +7$).

EXAMPLE 2A

3''-desmethoxy-22,23-dihydro-4''-oxo-avermectin B1a/B1b

A solution of 3''-desmethoxy-22,23-dihydro-4''-oxo-5-O-tert-butyldimethylsilyl avermectin B1a/B1b (300 mg.) in methanol (5 mL.) at 0° C. is treated with a 1% solution of p-toluenesulfonic acid in methanol (5 mL.) in accordance with the procedure fully described in example 2 to afford 3''-desmethoxy-22,23-dihydro-4''-oxo-avermectin B1a/B1b.

EXAMPLE 3

3''-desmethoxy-avermectin $B_1$ and 3''-desmethoxy-4''-epi-avermectin B1a/B1b

To stirred solution of 3''-desmethoxy-4''-oxo-avermectin B1a/B1b (19 mg., 0.023 mmol., 1 eq.) in methanol (1 mL.) in a 10 mL. round bottom flask equipped with a stir bar at 0° C. was added a solution of $NaBH_4$ in ethanol (0.090 mL., 0.045 mmol., 2 eq., 0.5M). The mixture was stirred for 15 min at 0° C. and then quenched with saturated aqueous $NaHCO_3$ and extracted 5x with $CH_2Cl_2$. The organic extracts were combined, dried over anhydrous $Na_2CO_3$, filtered, concentrated in vacuo and separated by preparative TLC on silica gel (eluted with 3.5% methanol/$CH_2Cl_2$) to afford 3.7 mg. 3''-desmethoxy-4''-epi avermectin B1a/B1b ($R_f$=0.26) and 11.4 mg 3''-desmethoxy avermectin B1a/B1b ($R_f$=0.20) characterized by $^1H$ NMR and mass spectral analysis. 3''-Desmethoxy-4''-epi avermectin B1a/B1b selected $^1H$ NMR data (300 MHz)($CDCl_3$) $CHCl_3$:1.25(3H, d, J=7 Hz, C5'Me); 1.15(3H, d, J=7 Hz, C5''Me); 1.14(3H, d, J=7 Hz, C24Me). Mass spectrum (FAB)(Li spike): 849($M^+ +7$). 3''-Desmethoxy avermectin B1a/B1b selected $^1H$ NMR data (300 MHz)($CDCl_3$) $CHCl_3$: 1.26(3H, d, J=6.5 Hz, C5'Me); 1.22(3H, d, J=6.5 Hz, C5''Me); 1.13(3H, d, J=6.5 Hz, C24Me). Mass spectrum (FAB)(Li spike): 849($M^{30} +7$).

EXAMPLE 3A

3''-desmethoxy-22,23-dihydro-avermectin B1a/B1b and 3''-desmethoxy-22,23-dihydro-4''-epi-avermectin B1a/B1b A solution of 3''-desmethoxy-22,23-dihydro-4''-oxo-avermectin B1a/B1b (19 mg) in methanol (1 mL.) at 0° C. is treated with a 0.5M solution of $NaBH_4$ in ethanol (0.09 mL.) in accordance with the procedure fully described in example 3 to give 3''-desmethoxy-22,23-dihydro-avermectin B1a/B1b and 3''-desmethoxy-22,23-dihydro-4''-epi-avermectin B1a/B1b.

EXAMPLE 4

5-O-tert-butyldimethylsilyl-4'-O-tetrahydropyranyl-avermectin B1a/B1b monosaccharide To a stirred solution of 5-O-tert-butyldimethylsilyl avermectin B1a/B1b monosaccharide (15 mg., 0.018 mmol., 1 eq.) in $CH_2Cl_2$ (0.5 ml.) in a 15 mL. round bottom flask equipped with a stir bar was added dihydropyran (0.003 ml., 0.021 mmol., 1.2 eq.) followed by addition of a solution of p-toluene-sulfonic acid in $CH_2Cl_2$ (0.180 ml., 0.002 mmol., 0.1 eq., 0.1M). The mixture was stirred for 2.5 h under $N_2$ and then quenched with saturated aqueous $NaHCO_3$ and extracted 4x with $CH_2Cl_2$. The organic extracts were combined, dried over anhydrous $Na_2SO_4$, filtered, concentrated in vacuo, and separated by preparative TLC on silica gel (eluted with 3:1 hexanes/actone) to afford 14.1 mg 5-O-tert-butyldimethylsilyl-4'-O-tetrahydropyranyl- avermectin B1a/B1b monosaccharide characterized by $^1$H NMR spectroscopy.

EXAMPLE 5

4'-O-tetrahydropyranyl-avermectin B1a/B1b monosaccharide

To a polyethylene centrifuge tube containing 5-O-tert-butyldimethylsilyl-4'-O-tetrahydropyranyl-avermectin B$_1$ monosaccharide (14.1 mg.) and equipped with a stir bar was added a solution of HF and pyridine in THF (0.5 mL. of a solution of 20 mL HF.pyridine+60 mL. pyridine+120 mL THF). The tube was capped and the reaction mixture was stirred overnight. The reaction mixture was quenched carefully by dropwise addition of saturated aqueous NaHCO$_3$. The mixture was diluted with aqueous NaHCO$_3$ and extracted 4x with CH$_2$Cl$_2$. The organic extracts were combined, dried over anhydrous Na$_2$SO$_4$, filtered, concentrated in vacuo, and separated by preparative TLC on silica gel (eluted with 3:1 hexanes/acetone) to afford 5.2 mg 4'-O-tetrahydropyranyl-avermectin B1a/B1b monosaccharide characterized by $^1$H NMR and mass spectral analysis. Selected $^1$H NMR data (300 MHz)(CDCl$_3$) δ CHCl$_3$: 4.9–5.0(2H, m, H15+H1''); 4.75(1H, d, J=3.7, H1'); 4.28(1H, t, J=6, H5); 3.45(3H, s, OH3); 3.28(2H, m, H4'+H2). Mass spectrum (FAB)-(Li spike): 819(M++7).

EXAMPLE 6

3''-desmethoxy-4''deoxo-4''-methylamino-5O-tert-butyldimethylsilyl-avermectin B1a/B1b and 3''-desmethoxy-4''-deoxo-4''-epi-methylamino-5-O-tert-butyldimethylsilyl-avermectin B1a/B1b To a strirred solution of 3''-desmethoxy-4''-oxo-5-O-tert-butyldimethylsilyl-avermectin B1a/B1b (50 mg., 0.053 mmol., 1 eq.) in methanol (2 mL) in a 16 mL. screw-cap vial equipped with a stir bar was added methylamine hydrochloride (35 mg., 0.52 mmol., 10 eq.) followed by addition of diisopropylethylamine (0.045 mL., 0.26 mmol., 5 eq.). To the stirred mixture was added NaCNBH$_3$ (8 mg., 0.127 mmol., 2.4 eq). The vial was capped and the mixture stirred for 1.5 h. The reaction mixture was quenched with saturated aqueous NaHCO$_3$ and extracted 4x with CH$_2$Cl$_2$. The organic extracts were combined, dried over anhydrous Na$_2$SO$_4$, filtered, concentrated in vacuo, and separated by preparative TLC on silica gel (eluted with 3:1 hexanes/acetone) to afford 12.8 mg 3''-desmethoxy-4''-deoxo-4''-methylamino-5-O-tert-butyldimethylsilyl-avermectin B1a/B1b (R$_f$=0.15) and 6.7 mg. 3''-desmethoxy-4''-deoxo-4''-epi-methylamino-5-O-tert-butyldimethylsilyl-avermectin B$_1$ (R$_f$=0.05) characterized by $^1$H NMR spectroscopy.

EXAMPLE 6A

3''-desmethoxy-4''-deoxo-22,23-dihydro-4''-methylamino-5-O-tert-butyldimethylsilyl-avermectin B1a/B1b and 3''-des-methoxy-4''-deoxo-22,23-dihydro-4''-epi-methylamino-5-O-tert-butyldimethylsilyl-avermectin B1a/B1b A solution of 3''-desmethoxy-22,23-dihydro-4''-oxo-5-O-tert-butyldimethylsilyl-avermectin B1a/B1b (50 mg.) in methanol is treated with methylamine hydrochloride (35 mg.), diisopropylamine (0.045 mL.), and sodium cyanoborohydride (8 mg) in accordance with the procedure fully described in example 6 to give 3''-desmethoxy-4''-deoxo-22,23-dihydro-4''-methylamino-5-O-tert-butyldimethylsilyl-avermectin B1a/B1b and 3''-desmethoxy-4''-deoxo-22,23-dihydro-4''-epi-methylamino-5-O-tert-butyldimethylsilyl-avermectin B1a/B1b.

EXAMPLE 7

3''-desmethoxy-4''-deoxo-4''-methylamino-avermectin B1a/B1b

To a polypropylene centrifuge tube containing 3''-desmethoxy-4''-deoxo-4''-methylamino-5-O-tert-butyldimethylsilyl avermectin B1a/B1b (12.8 mg.) and equipped with a stir bar was added a solution of HF.pyridine in THF (0.5 mL. of a solution of 15 mL HF.pyridine+60 mL. pyridine+120 mL THF). The tube was capped and the mixture stirred overnight. The reaction was carefully quenched with saturated aqueous NaHCO$_3$ and extracted 4× with CH$_2$Cl$_2$. The organic extracts were combined, dried over anhydrous Na$_2$SO$_4$, filtered, concentrated in vacuo, and separated by preparative TLC on silica gel (eluted with 7% methanol/CH$_2$Cl$_2$) to afford 3.6 mg. 3''-desmethoxy-4''-deoxo-4''-methylamino-avermectin B1a/B1b characterized by $^1$H NMR and mass spectral analysis.

EXAMPLE 7A

3''-desmethoxy-22,23-dihydro-4''-deoxo-4''-methylamino-avermectin B1a/B1b

3''-desmethoxy-4''-deoxo-22,23-dihydro-4''-methylamino-5-O-tert-butyldimethylsilyl-avermectin B1a/B1b (12.8 mg) is treated with a solution of HF.pyridine in tetrahydrofuran (0.5 mL. of a solution of 15 mL. HF.pyridine plus 45 mL. pyridine plus 120 mL. tetrahydrofuran) in accordance with the procedure fully described in example 7 to afford 3''-desmethoxy-22,23-dihydro-4''-deoxo-4''-methylamino-avermectin B1a/B1b.

EXAMPLE 8

3''-desmethoxy-4''-deoxo-4''-epi-methylamino-avermectin B1a/B1b

To a polypropylene centrifuge tube containing 3''-desmethoxy-4''-deoxo-4''-epi-methylamino-5-O-tert-butyldimethylsilyl avermectin B1a/B1b (6.7 mg.) and equipped with a stir bar was added a solution of HF.pyridine in THF (0.5 mL. of a solution of 15 mL HF.pyridine+60 mL. pyridine+120 mL THF). The tube was capped and the mixture stirred overnight. The reaction was carefully quenched with saturated aqueous NaHCO$_3$ and extracted 4× with CH$_2$Cl$_2$. The organic extracts were combined, dried over anhydrous Na$_2$SO$_4$, filtered, concentrated in vacuo, separated by preparative TLC on silica gel (eluted 2× with 7% methanol/CH$_2$Cl$_2$) to afford 2.1 mg. 3''-desmethoxy-4''-deoxo-4''-epi-methylamino-avermectin B1a/B1b characterized by $^1$H NMR and mass spectral analysis.

EXAMPLE 9

4''-amino-4''-deoxo-3''-desmethoxy-5-O-tert-butyldimethylsilyl-avermectin B1a/B1b and 4''-deoxo-3''-desmethoxy-4''-epi-amino-5-O-tert-butyldimethylsilyl-avermectin B1a/B1b To a stirred solution of 3''-desmethoxy-4''-oxo-5-O-tert-butyldimethylsilyl-avermectin B1 (175 mg, 0.184 mmol., 1 eq.) in methanol (3.5 mL.) in a 25 mL. pear-shaped flask equipped with a stir bar was added NH$_4$OAc (170 mg., 2.21 mmol., 12 eq.) followed by addition of NaCNBH$_3$ (52 mg., 0.829 mmol., 4.5 eq.). The reaction mixture was stirred for 1.3 h under N$_2$. The reaction was quenched with saturated aqueous NaHCO$_3$ and extracted 5× with CH$_2$Cl$_2$. The organic extracts were combined, dried over anhydrous Na$_2$SO$_4$, concentrated in vacuo, and separated by preparative TLC on silica gel (eluted with 3.5% methanol/CH$_2$Cl$_2$) to afford 37.3 mg. 4''-amino-4''-deoxo-3''-desmethoxy-5-O-tert-butyldimethylsilyl-avermectin B1a/B1b ($R_f$=0.28) and 7.2 mg. 4''-deoxo-3''-desmethoxy-4''-epi-amino-5-O-tert-butyl-dimethylsilyl-avermectin B1a/B1b ($R_f$=0.09) characterized by $^1$H NMR spectroscopy.

EXAMPLE 10

4''-amino-4''-deoxo-3''-desmethoxy-avermectin B1a/B1b

To a polypropylene centrifuge tube containing 4''-amino-4''-deoxo-3''-desmethoxy-5-O-tert-butyldimethylsilyl-avermectin B1a/B1b (37.3 mg.), and equipped with a stir bar was added a solution of HF.pyridine in THF (1.0 mL. of a solution of 15 mL HF.pyridine+60 mL. pyridine+120 mL THF). The tube was capped and the mixture stirred for 6 h. The reaction was carefully quenched with saturated aqueous NaHCO$_3$ and extracted 4× with CH$_2$Cl$_2$. The organic extracts were combined, dried over anhydrous Na$_2$O$_4$, filtered, concentrated in vacuo, and separated by preparative TLC on silica gel (eluted 2× with 7% methanol/CH$_2$Cl$_2$) to afford 16.2 mg. 4''-amino-4''-deoxo-3''-desmethoxy-avermectin B1a/B1b characterized by $^1$H NMR and mass spectral analysis.

EXAMPLE 11

4''-deoxo-3''-desmethoxy-4''-epi-amino-avermectin B1a/B1b

To a polypropylene centrifuge tube containing 4''-deoxo-3''-desmethoxy-4''-epi-amino-5-O-tert-butyl-dimethylsilyl-avermectin B1a/B1b (7.2 mg.), and equipped with a stir bar was added a solution of HF.pyridine in THF (0.5 mL. of a solution of 15 mL HF.pyridine+60 mL. pyridine+120 mL THF). The tube was capped and the mixture stirred for 6 h. The reaction was carefully quenched with saturated aqueous NaHCO$_3$ and extracted 4× with CH$_2$Cl$_2$. The organic extracts were combined, dried over anhydrous Na$_2$SO$_4$, filtered, concentrated in vacuo, and separated by preparative TLC on silica gel (eluted 2× with 7% methanol/CH$_2$Cl$_2$) to afford 2.4 mg. 4''-deoxo-3''-desmethoxy-4''-epi-amino-avermectin B1a/B1b characterized by $^1$H NMR and mass spectral analysis.

EXAMPLE 12

4''-acetylamino-4''-deoxo-3''-desmethoxy-avermectin B1a/B1b

To a stirred solution of 4''-amino-4''-deoxo-3''-desmethoxy-avermectin B1a/B1b (16.1 mg., 0.019 mmol., 1 eq.) in CH$_2$Cl$_2$(0.20 mL.) in a 10 mL. recovery flask equipped with a stir bar was added a solution of acetic anhydride in CH$_2$Cl$_2$ (0.020 mL., 0.021 mmol., 1.1 eq., 10% solution). The mixture was stirred for 1 h, then diluted with saturated aqueous NaHCO$_3$ and extracted 4× with CH$_2$Cl$_2$. The organic extracts were combined, dried over anhydrous Na$_2$SO$_4$, filtered, concentrated in vacuo and separated by preparative TLC on silica gel (eluted with 3.5% methanol/CH$_2$Cl$_2$ to afford 12.9 mg 4''-acetylamino-4''-deoxo-3''-desmethoxy-avermectin B1a/B1b characterized by $^1$H NMR and mass spectral analysis.

EXAMPLE 13

4''-deoxo-3''-desmethoxy-4''-epi-acetylamino-avermectin B1a/B1b

To a stirred solution of 4''-deoxo-3''-desmethoxy-4''-epi-amino-avermectin B1a/B1b (3.1 mg., 0.003 mmol., 1 eq.) in CH$_2$Cl$_2$ (0.20 mL.) in a 10 mL. recovery flask equipped with a stir bar was added a solution of acetic anhydride in CH$_2$Cl$_2$ (0.10 mL., 0.010 mmol., 3.3 eq., 10% solution). The mixture was stirred for 1 h, then diluted with saturated aqueous NaHCO$_3$ and extracted 4× with CH$_2$Cl$_2$. The organic extracts were combined, dried over anhydrous Na$_2$SO$_4$, filtered, concentrated in vacuo and separated by preparative TLC on silica gel (eluted with 3.5% methanol/CH$_2$Cl$_2$ to afford 2.7 mg 4''-deoxo-3''-desmethoxy-4''-epi-acetylamino-avermectin B1a/B1b characterized by $^1$H NMR and mass spectral analysis.

EXAMPLE 14

3''-desmethoxy avermectin B1a/B1b-4''-semicarbazone

To a stirred solution of 3''-desmethoxy-4''-oxo-avermectin B1a/B1b (26.7 mg., 0.032 mmol., 1 eq.) in methanol (2 mL.) in a 50 mL. round bottom flask equipped with a stir bar was added semicarbazide hydrochloride (30 mg., 0,269 mmol., 8.4 eq.) followed by addition of 2 drops pyridine. The mixture was stirred 5 h, then diluted with saturated aqueous NaHCO$_3$ and extracted 5× with CH$_2$Cl$_2$. The organic extracts were combined, dried over anhydrous Na$_2$SO$_4$, filtered, concentrated in vacuo, and separated by preparative TLC on silica gel (eluted with 7% methanol/CH$_2$Cl$_2$) to afford 18.5 mg. 3''-desmethoxy avermectin B1a/B1b-4''-semicarbazone characteried by $^1$H NMR and mass spectral analysis.

EXAMPLE 15

3'-desmethoxy-4'-oxo-5-O-tert-butyldimethyl avermectin B1a/B1b monosaccharide

A solution of 4'-oxo-5-O-tert-butyldimethylsilyl avermectin B1a/B1b monosaccharide (1.67 g) and methanol (2 mL.) in tetrahydrofuran (110 mL.) is reacted with samarium diiodide solution in tetrahydrofuran (110 mL., 0.04M solution) in accordance with the procedure described fully in example 1 to give 3'-desmethoxy-4'-oxo-5-O-tert-butyldimethyl avermectin B1a/B1b monosaccharide.

EXAMPLE 16

3'-desmethoxy-4'-oxo-avermectin B1a/B1b monosaccharide

A solution of 3'-desmethoxy-4'-oxo-5-O-tert-butyldimethylsilyl avermectin B1a/B1b monosaccharide (300 mg.) in methanol (5 mL.) at 0° C. is treated with a 1% solution of p-toluenesulfonic acid in methanol (5 mL.) in accordance with the procedure fully described in example 2 to afford 3'-desmethoxy-4'-oxo-avermectin B1a/B1b monosaccharide.

EXAMPLE 17

3'-desmethoxy-4'-deoxo-4'-methylamino-5-O-tert-butyldimethylsilyl-avermectin B1a/B1b monosaccharide and
3'-desmethoxy-4'-deoxo-4'-epi-methylamino-5-O-tert-butyldimethylsilyl-avermectin B1a/B1b monosaccharide A solution of 3'-desmethoxy-4'-oxo-5-O-tert-butyldimethylsilyl-avermectin B1a/B1b monosaccharide (50 mg.) in methanol is treated with methylamine hydrochloride (35 mg.), diisopropylamine (0.045 mL.), and sodium cyanoborohydride (8 mg) in accordance with the procedure fully described in example 6 to give 3'-desmethoxy-4'-deoxy-4'-methylamino-5-O-tert-butyldimethylsilyl-avermectin B1a/B1b monosaccharide and 3'-desmethoxy-4'-deoxo-4'-epi-methylamino-5-O-tert-butyldimethylsilyl-avermectin B1a/B1b monosaccharide.

EXAMPLE 18

3'-desmethoxy-4'-deoxo-4'-methylamino-avermectin B1a/B1b monosaccharide

3'-desmethoxy-4'-deoxo-4'-methylamino-5-O-tert-buytyldimethylsilyl-avermectin B1a/B1b monosaccharide (12.8 mg) is treated with a solution of HF.pyridine in tetrahydrofuran (0.5 mL. of a solution of 15 mL. HF.pyridine plus 45 mL. pyridine plus 120 mL. tetrahydrofuran) in accordance with the procedure fully described in example 7 to afford 3'-desmethoxy-4'-deoxo-4'-methylamino-avermectin B1 monosaccharide.

EXAMPLE 19

22,23-dihydro-4''-O-(4-methylphenoxythionocarbonyl)-5-O-t-butyldimethylsilyl avermectin B1a/B1b To a stirred solution of 22,23-dihydro-5-O-t-butyldimethylsilyl avermectin B1a/B1b (500 mg) in acetonitrile (15 mL.) was added dimethylaminopyridine (600 mg.) and O-4-methylphenyl chlorothioformate (0.400 mL). The mixture was stirred at room temperature under N₂ for 1.5 h. An additional 100 mg. of dimethylaminopyridine was added and the mixture was stirred overnight at room temperature under N₂. The reaction was quenched by pouring into water and the mixture was acidified by addition of 2.5N aqueous HCl. The mixture was extracted 3× with ethyl acetate. The organic fractions were combined and washed 1× with dilute HCl, 2× with water, and 1× with brine. The organic phase was concentrated in vacuo and the residue purified by preparative TLC on silica gel (eluted with 3% ethyl acetate in methylene chloride) to afford 280 mg 22,23-dihydro-4''-O-(4-methylphenoxythionocarbonyl)-5-O-t-butyldimethylsilyl avermectin B1a/B1b characterized by ¹H NMR and mass spectral analysis.

EXAMPLE 20

22,23-dihydro-4''-O-(4-methylphenoxythionocarbonyl)-avermectin B1a/B1b

To a test tube containing 22,23-dihydro-4''-O-(4-methylphenoxythionocarbonyl)-5-O-t-butyldimethylsilyl avermectin B1a/B1b (50 mg.) was added a solution of p-toluenesulfonic acid monohydrate and water in methanol (6 mL., 1% w/v p-toluenesulfonic acid in methanol plus 1 mL water). The mixture was stirred for 40 min at room temperature. The reaction was quenched with dilute NaHCO₃ and extracted 3× with ethyl acetate. The organic extracts were combined, washed with dilute aqueous NaCl, water then saturated aqueous NaCl, dried over MgSO₄, filtered and concentrated in vacuo affording 40 mg 22,23-dihydro-4''-O-(4-methylphenoxythionocarbonyl)-avermectin B1a/B1b characterized by ¹H NMR and mass spectral analysis.

EXAMPLE 21

4''-deoxo-22,23-dihydro-avermectin B1a/B1b

To a stirred solution of 22,23-dihydro-4''-O-(4-methylphenoxythionocarbonyl)-avermectin B1a/B1b (40 mg.) in toluene (2 mL.) was added azobisisobutyronitrile (10 mg.). The flask was fitted with a reflux condenser and placed under N₂. The reaction flask was immersed in an oil bath preheated to 120° C. To the mixture maintained at gentle reflux was added a solution of tri-n-butyltin hydride (0.200 mL.) in toluene (2 mL.) via pipette. After maintaining reaction at reflux for 35 min the the heating element in the oil bath was turned off and the solvent in the reaction mixture was removed by a stream of N₂. The residue was diluted with CH₂Cl₂ and the product isolated by preparative TLC on silica gel (eluted with 10% ethyl acetate/CH₂Cl₂) to afford 20.9 mg. 4''-deoxo-22,23-dihydro-avermectin B1a/B1b characterized by ¹H NMR and mass spectral analysis.

EXAMPLE 22

5-O-tert-Butyldimethylsilyl-avermectin B2a/B2b

To a stirred solution of avermectin B2a/B2b (100 mg.) in dry dimethylformamide (1 mL.) is added tert-butyldimethylsilylchloride (48 mg.) and imidazole (48 mg.) and the mixture is stirred at room temperature for 50 minutes. The reaction mixture is then diluted with water and extracted 3× with CH₂Cl₂. The organic extracts are combined, dried over anhydrous Na₂SO₄, filtered and concentrated in vacuo. The product mixture is separated by silica gel column chromatography with a CH₂Cl₂-EtOAc 90:10 to 70:30 solvent system to give 5-O-tert-Butyldimethylsilyl-avermectin B2a/B2b.

EXAMPLE 23

4''-oxo-5-O-tert-butyldimethylsilyl-avermectin B2a/B2b

To a dried flask purged with N₂ is added oxalyl chloride (0.097 mL.) and CH₂Cl₂ (1.5 mL.). The reaction mixture is cooled to −78° C. and a solution of dimethylsulfoxide (0.169 mL.) in CH₂Cl₂ (1 mL.) is added over 3 min and the reaction mixture is stirred for two minutes at −78° C. To the reaction mixture is added a solution of 5-O-tert-Butyldimethylsilyl-avermectin B₂ (500 mg.) in CH₂Cl₂ (3 mL.) dropwise over 5 minutes and the mixture is stirred at −78° C. for 30 minutes. At the end of this period triethylamine (0.71 mL.) is added dropwise and the reaction mixture is allowed is stirred at −78° C. for 5 minutes. The cooling bath is removed and the reaction is allowed to come to room temperature over a period of 45 minutes. The reaction is quenched by addition of 50 mL. of water and is extracted 4× with $CH_2Cl_2$. The organic extracts are combined, dried over anhydrous $Na_2SO_4$, filtered, and concentrated in vacuo. The product mixture is separated by preparative TLC on silica gel to afford 4''-oxo-5-O-tert-butyldimethylsilyl-avermectin B2a/B2b 23-oxo-5-O-tert-butyldimethylsilyl-avermectin B2a/B2b, and 4'',23-bis-oxo-5-O-tert-butyldimethylilyl-avermectin B2a/B2b.

EXAMPLE 24

3''-desmethoxy-4''-oxo-5-O-tert-butyldimethylsilyl-avermectin B2a/B2b

A solution of 4''-oxo-5-O-tert-butyldimethylsilyl-avermectin B2a/B2b (1.96 g) and methanol (2 mL.) in Tetrahydrofuran (110 mL.) is reacted with samarium diiodide solution in tetrahydrofuran (110 mL., 0.04M solution) in accordance with the procedure described fully in example 1 to give 3''-desmethoxy-4''-oxo-5-O-tert-butyldimethylsilyl-avermectin B2a/B2b.

EXAMPLE 25

4''-amino-4''-deoxo-3''-desmethoxy-5-O-tert-butyldimethylsilyl-avermectin B2a/B2b and
4''-deoxo-3''-desmethoxy-4''-epi-amino-5-O-tert-butyldimethylsilyl-avermectin B2a/B2b A stirred solution of 3''-desmethoxy-4''-oxo-5-O-tert-butyldimethylsilyl-avermection B2a/B2b (175 mg.), methanol (3.5 mL.) and $NH_4OAc$ (170 mg.) is reacted with $NaCNBH_3$ (52 mg) in accordance with the procedure fully described in EXAMPLE 9 to afford 4''-amino-4''-deoxo-3''-desmethoxy-5-O-tert-butyldimethylsilyl-avermectin B2a/B2b and 4''-deoxo-3''-desmethoxy-4''-epi-amino-5-O-tert-butyldimethylsilyl-avermectin B2a/B2b.

EXAMPLE 26

4''-amino-4''-deoxo-3''-desmethoxy-avermectin B2a/B2b

4''-amino-4''-deoxo-3''-desmethoxy-5-O-tert-butyldimethylsilyl-avermectin $B_2$ (37.3 mg.) is treated with a solution of HF.pyridine and pyridine in tetrahydrofuran (1.0 mL. of a solution of 15 mL HF.pyridine+60 mL. pyridine+120 mL THF) in accordance with the procedure fully described in EXAMPLE 10 to afford 4''-amino-4''-deoxo-3''-desmethoxy-avermectin B2a/B2b.

EXAMPLE 27

25-cyclopentyl-25-de-(1-methylpropyl)-5-O-tert-butyldimethylsilyl-avermectin B1a A solution of 25-cyclopentyl-25-de-(1-methylpropyl)-avermectin B1a (100 mg).), imidazole (48 mg.), tert-butyldomethylsilylchloride (48 mg.) in dry dimethylformamide (1.0 mL.) is treated in accordance with the procedure fully described in EXAMPLE 22 to afford 25-cyclopentyl-25-de-(1-methylpropyl)-5-O-tert-butyldimethylsilyl-avermectin B1a.

EXAMPLE 28

25-cyclopentyl-25-de-(1-methylpropyl)-5-O-tert-butyldimethylsilyl-4''-oxo-avermectin B1a To a dried flask purged with $N_2$ is added oxalyl chloride (0.097 mL.) and $CH_2Cl_2$ (1.5 mL.). The reaction mixture is cooled to −78° C. and a solution of dimethylsulfoxide (0.169 mL.) in $CH_2Cl_2$ (1 mL.) is added over 3 min and the reaction mixture is stirred for two minutes at −78° C. To the reaction mixture is added a solution of 25-cyclopentyl-25-de-(1-methylpropyl)-5-O-tert-butyldimethylsilyl-avermectin B1a (500 mg.) in $CH_2Cl_2$ (3 mL.) dropwise over 5 minutes and the mixture is stirred at −78° C. for 30 minutes. At the end of this period triethylamine (0.71 mL.) is added dropwise and the reaction mixture is allowed is stirred at −78° C. for 5 minutes. The cooling bath is removed and the reaction is allowed to come to room temperature over a period of 45 minutes. The reaction is quenched by addition of 50 mL. of water and is extracted 4x with $CH_2Cl_2$. The organic extracts are combined, dried over anhydrous $Na_2SO_4$, filtered, and concentrated in vacuo. The product mixture is separated by preparative TLC on silica gel to afford 25-cyclopentyl-25-de-(1-methylpropyl)-5-O-tert-butyldimethylsilyl-4''-oxo-avermectin B1a.

EXAMPLE 29

25-cyclopentyl-25-de-(1-methylpropyl)-3''-desmethoxy-4''-oxo-5-O-tert-butyldimethylsilyl-avermectin B2a A solution of 25-cyclopentyl-25-de-(1-methylpropyl)-5-O-tert-butyldimethylsilyl-4''-oxo-avermectin B1a (1.96 g) and methanol (2 mL.) in tetrahydrofuran (110 mL.) is reacted with samarium diiodide solution in tetrahydrofuran (110 mL., 0.04M solution) in accordance with the procedure described fully in example 1 to give 25-cyclopentyl-25-de-(1-methylpropyl)-3''-desmethoxy-4''-oxo-5-O-tert-butyldimethylsilyl-avermectin B2a.

EXAMPLE 30

25-cyclopentyl-25-de-(1-methylpropyl)-3''-desmethoxy-4''-oxo-avermectin B2a

A solution of 25-cyclopentyl-25-de-(1-methylpropyl)-3''-desmethoxy-4''-oxo-5-O-tert-butyldimethylsilyl-avermectin B2a (300 mg.) in methanol (5 mL.) at 0° C. is treated with a 1% solution of p-toluenesulfonic acid in methanol (5mL.) in accordance with the procedure fully described in example 2 to afford 25-cyclopentyl-25-de-(1-methylpropyl)-3''-desmethoxy-4''-oxo-avermectin B2a.

EXAMPLE 31

25-cylopentyl-25-de-(1-methylpropyl)-3''-desmethoxy-avermectin B1a and
25-cyclopentyl-25-de-(1-methylpropyl)-3''-desmethoxy-4''-epi-avermectin B1a A stirred solution of 25-cyclopentyl-25-de-(1-methylpropyl)-3''-desmethoxy-4''-oxo-avermectin B1a (19 mg.) in methanol (1 mL.) is treated with an ethanolic solution of $NaBH_4$ in accordance with the procedure fully described in EXAMPLE 3 to afford 25-cyclopentyl-25-de-(1-methylpropyl)-3''-desmethoxy-avermectin B1a and 25-cyclopentyl-25-de-(1-methylpropyl)-3''-desmethoxy-4''-epi-avermectin B1a.

What is claimed is:

1. A compound having the formula:

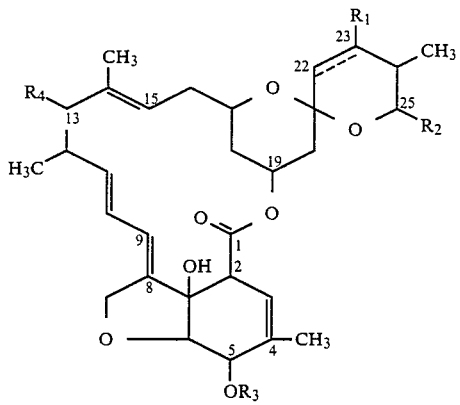

wherein the broken line at the 22,23 position represents a 22,23-single bond and wherein $R_1$ is hydrogen, hydroxy or keto, or the broken line represents a 22,23-double bond and $R_1$ is absent;

$R_2$ is an alpha branched $C_3-C_8$ alkyl or alkenyl group;
$R_3$ is hydrogen, loweralkyl or loweralkanoyl;
$R_4$ is

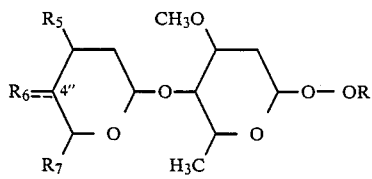

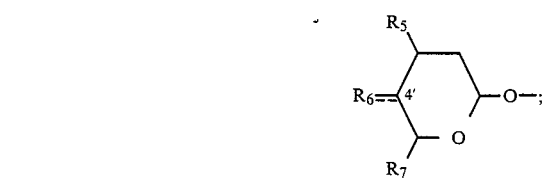

$R_5$ is hydrogen and $R_6$ is hydroxy, amino, N-loweralkylamino, N,N-diloweralkylamino, loweralkanoylamino, or N,N-diloweralkylalkanoylamino when the broken line to $R_6$ indicates a 4' or 4" single bond or $R_6$ is keto, semicarbazone, N-loweralkylsemicarbazone, N,N-diloweralkylsemicarbazone, oxime, or loweralkyloxime when the broken line to $R_6$ indicates a 4" or 4" double bond; or $R_5$ is hydrogen or methoxy and $R_6$ is hydrogen; and $R_7$ is methyl or hydrogen.

2. A compound of claim 1 wherein the broken line at the 22,23 position represents a 22,23-single bond and wherein $R_1$ is hydrogen or hydroxy, or the broken line represents a 22,23-double bond and $R_1$ is absent;

$R_2$ is iso-propyl, sec-butyl, or an alpha-branched $C_3-C_8$ alkenyl group;
$R_3$ is hydrogen;
$R_4$ is

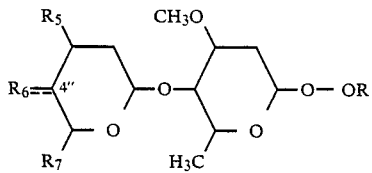

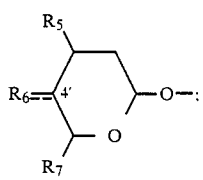

$R_5$ is hydrogen and $R_6$ is hydroxy, amino, N-loweralkylamino, loweralkanoylamino, or N,N-diloweralkyl-alkanoylamino when the broken line to $R_6$ indicates a 4' or 4" single bond or $R_6$ is keto, semicarbazone, N-loweralkylsemicarbazone, N,N-diloweralkylsemicarbazone, or oxime, when the broken line to $R_6$ indicates a 4' or 4" double bond; or $R_5$ is hydrogen or methoxy and $R_6$ is hydrogen; and $R_7$ is methyl or hydrogen.

3. A compound of claim 1 wherein the broken line at the 22,23 position represents a single bond and wherein $R_1$ is hydrogen or hydroxy, or the broken line represents a double bond and $R_1$ is absent;

$R_2$ is iso-propyl, sec-butyl, or an alpha-branched $C_3-C_8$ alkenyl group;
$R_3$ is hydrogen;
$R_4$ is

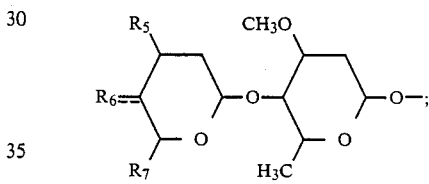

$R_5$ is hydrogen;
$R_6$ is hydroxy, amino, N-loweralkylamino, loweralkanoylamino, N,N-diloweralkylalkanoylamino when the broken line to $R_6$ indicates a 4" single bond or $R_6$ is keto, semicarbazone, N-loweralkylsemicarbazone, N,N-diloweralkylsemicarbazone, or oxime when the broken line to $R_6$ indicates a 4" double bond; and $R_7$ is methyl or hydrogen.

4. The compound of claim 1 which is 4"-oxo-3"-desmethoxy avermectin B1a/B1b.

5. The compound of claim 1 which is 3"-desmethoxy-4"-epi avermectin B1a/B1b.

6. The compound of claim 1 which is 3"-desmethoxy avermectin B1a/B1b.

7. The compound of claim 1 which is 4'-O-tetrahydropyranyl-avermectin B1a/B1b monosaccharide.

8. The compound of claim 1 which is 3"-desmethoxy-4"-deoxo-4"-methylamino-avermectin B1a/B1b.

9. The compound of claim 1 which is 3"-desmethoxy-4"-deoxo-22,23-dihydro 4"-epi-methylamino-avermectin B1a/B1b.

10. The compound of claim 1 which is 4"-amino-4"-deoxo-3"-desmethoxy-avermectin B1a/B1b.

11. The compound of claim 1 which is 4"-deoxo-3"-desmethoxy-4"-epi-amino-avermectin B1a/B1b.

12. The compound of claim 1 which is 4"-acetylamino-4"-deoxo-3"-desmethoxy-avermectin B1a/B1b.

13. The compound of claim 1 which is 4"-deoxo-3"-desmethoxy-4"-epi-acetylamino-avermectin B1a/B1b.

14. The compound of claim 1 which is 3"-desmethoxy avermectin B1a/B1-4"-semicarbazone.

15. The compound of claim 1 which is 4"-deoxo-22,23-dihydro-avermectin B1a/B1b.

16. A composition useful for the treatment of parasitic diseases in animals which comprises an inert carrier and a compound of claim 1.

17. A method for the treatment of parasitic infestations of agricultural crops of growing or stored crops which comprises treating such growing crops or the soil in which they are growing or while such crops are in storage with an effective amount of a compound of claim 1.

18. A composition useful for the treatment of parasitic disease of agricultural crops which comprises an inert carrier and a compound of claim 1.

* * * * *